(12) United States Patent
Donovan et al.

(10) Patent No.: US 8,257,310 B2
(45) Date of Patent: Sep. 4, 2012

(54) DIGITAL SYRINGE WITH COMPENSATION CONTROL

(75) Inventors: Brian W. Donovan, San Jose, CA (US); Andrea Y. Leung, Milpitas, CA (US); Lisanne A. Eng, Campbell, CA (US); David P. Thompson, Mountain View, CA (US); Robert B. Hubler, Woodinville, WA (US); Stephanie A. Barnes, Redmond, WA (US); Thomas C. Arends, Bellevue, WA (US); Keith Schubert, Redmond, WA (US); Paul C. Leonard, Woodinville, WA (US); Paul F. Muller, San Carlos, CA (US)

(73) Assignee: Kyphon SARL, Neuchatel (CH)

( * ) Notice: Subject to any disclaimer, the term of this patent is extended or adjusted under 35 U.S.C. 154(b) by 0 days.

(21) Appl. No.: 13/196,256

(22) Filed: Aug. 2, 2011

(65) Prior Publication Data

US 2011/0288523 A1 Nov. 24, 2011

Related U.S. Application Data

(62) Division of application No. 12/386,971, filed on Apr. 24, 2009, now Pat. No. 8,002,748.

(51) Int. Cl.
*A61M 37/00* (2006.01)
*A61M 31/00* (2006.01)
(52) U.S. Cl. ........................ 604/154; 604/500
(58) Field of Classification Search ............... 604/154
See application file for complete search history.

(56) References Cited

U.S. PATENT DOCUMENTS

| 4,850,805 A * | 7/1989 | Madsen et al. ............... 417/18 |
| 2007/0112299 A1 * | 5/2007 | Smit et al. ..................... 604/67 |

* cited by examiner

*Primary Examiner* — Nicholas Lucchesi
*Assistant Examiner* — Jason Flick

(57) ABSTRACT

A syringe for performing a medical procedure includes a pressure sensor, a volume sensor, and a compensation circuit. The volume sensor measures a volume of a flowable material that is dispensed from the syringe, the pressure sensor measures a pressure being applied to the flowable material, and the compensation circuit calculates a delivered volume of the flowable material by accounting for system compliance (expansion) as the pressure is increased. By compensating for system compliance in this manner, a syringe can be used in high pressure procedures while still providing accurately controllable material delivery.

10 Claims, 11 Drawing Sheets

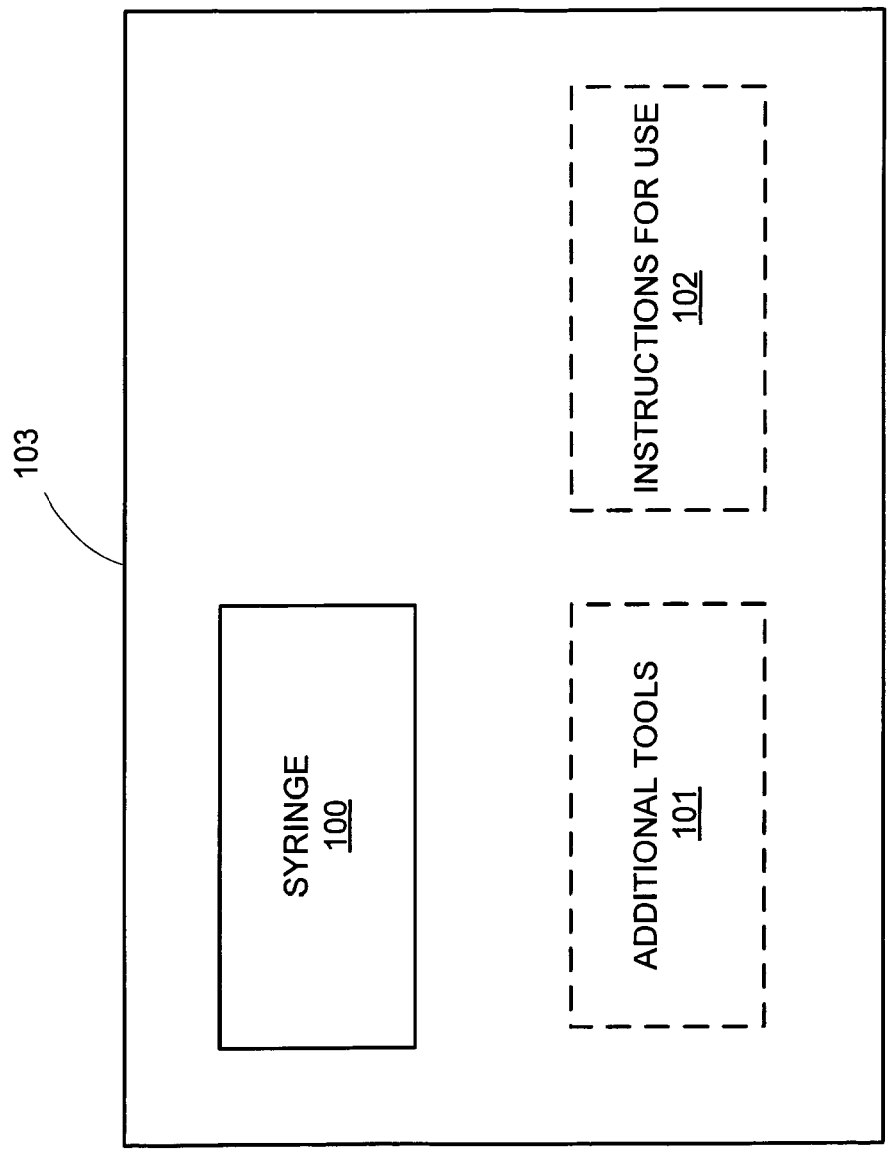

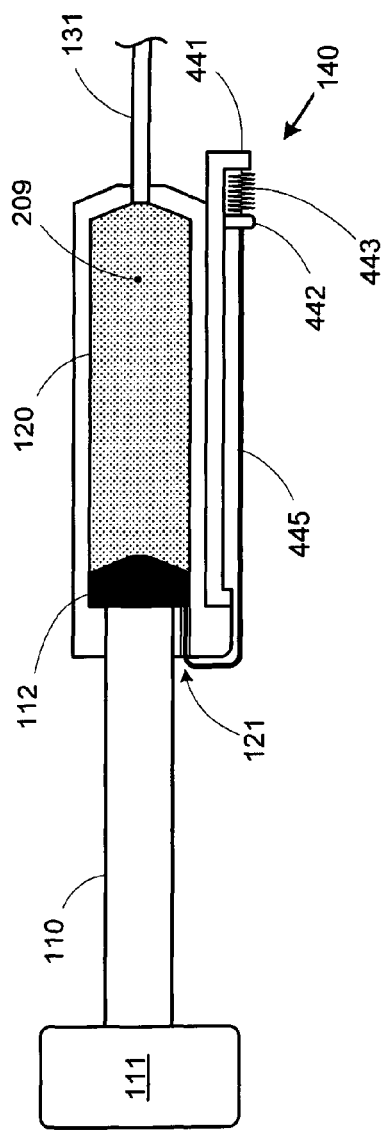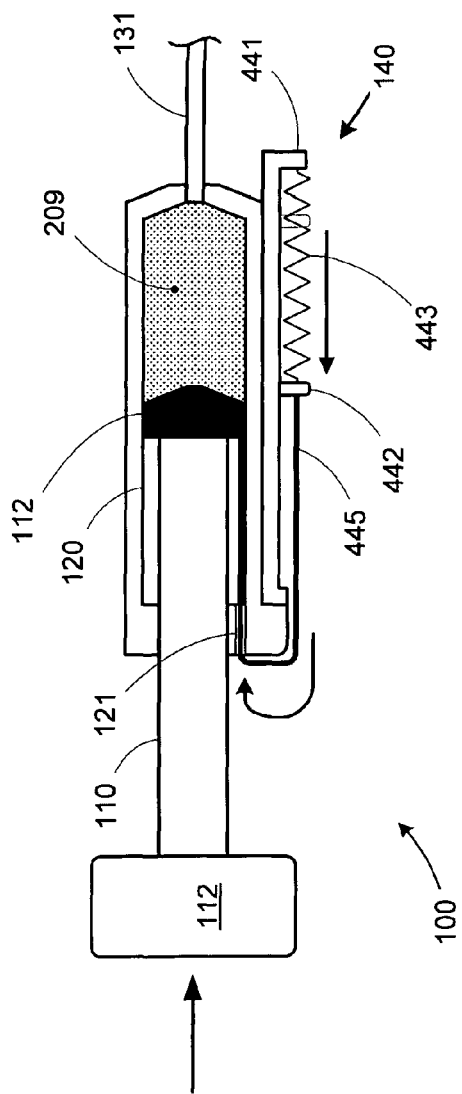
FIG. 4A
FIG. 4B

DIGITAL SYRINGE WITH COMPENSATION CONTROL

CROSS-REFERENCE

This application is a divisional of U.S. patent application Ser. No. 12/386,971 filed Apr. 24, 2009, attorney reference P0034574.00, the entire disclosure of which is incorporated herein by reference.

FIELD OF THE INVENTION

The invention relates to a system and method for performing a surgical procedure, and in particular, to a material delivery system that includes compensation logic for improving procedure accuracy.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Until recently, treatment options for vertebral compression fractures, as well as other serious fractures and/or losses in bone strength, were extremely limited—mainly pain management with strong oral or intravenous medications, reduced activity, bracing and/or radiation therapy, all with mediocre results. Because patients with these problems are typically older, and often suffer from various other significant health complications, many of these individuals are unable to tolerate invasive surgery. In addition, to curb further loss of bone strength, many patients are given hormones and/or vitamin/mineral supplements—again with mediocre results and often with significant side effects.

In an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

In many cases, enhancements to existing minimally invasive surgical procedures, or new applications for minimally invasive surgical procedures, necessitate the use of higher pressures to perform those procedures (e.g., the use of higher inflation pressures for inflatable bone tamps in kyphoplasty procedures to improve vertebral body height restoration capabilities). At the same time, it is also critical that process repeatability is maintained, or even improved, to ensure successful procedure outcomes. However, higher pressure systems often reduce performance accuracy, due to the compliance of system components. Therefore, the benefits provided by the enhanced capabilities of high pressure systems must be weighed against the increased difficulties in obtaining accurate measurements in such systems.

Accordingly, it is desirable to provide surgical tools and techniques that enable repeatable and controllable use of high pressure systems in surgical procedures.

SUMMARY OF THE INVENTION

By incorporating compensation logic into a material delivery system that accounts for system compliance, material delivery during surgical procedures can be accurately determined.

In one embodiment, a syringe includes a reservoir for holding flowable material, an actuator for dispensing the flowable material from the reservoir into a delivery path (e.g., a length of flexible tubing, a catheter, couplings, connectors, and anything else that provides a path for the flowable material), a volume sensor, a pressure sensor, and a compensation circuit. The volume sensor measures the volume of flowable material dispensed from the reservoir, the pressure sensor measures the pressure being applied to the flowable material, and the compensation circuit determines an actual volume of flowable material delivered to a delivery target (e.g., an expandable structure for manipulating bone).

In one embodiment, the compensation circuit can include lookup tables or mathematical models that provide the interior volume of the delivery path at various pressures. The compensation circuit can use the pressure provided by the pressure sensor to determine the interior volume of the delivery path components. The difference between the volume of flowable material dispensed from the reservoir (provided by the volume sensor) and the interior volume of the delivery path components can then be provided by the compensation circuit as the actual delivered volume of flowable material at the delivery target.

In various embodiments, the syringe can include a status indicator that provides an analog, digital, graphical, aural, or tactile indication of the actual delivered volume of flowable material at the delivery target and optionally the pressure being applied to the flowable material. In various other embodiments, the syringe can provide a warning (e.g., a visual, aural, or tactical indication) when the pressure sensor detects a threshold pressure, or when the compensation circuit indicates a threshold delivered volume of flowable material. In various other embodiments, the syringe can include an actuation controller that can stop the dispensing of flowable material when a threshold pressure or a threshold delivered volume of flowable material is detected.

In various other embodiments, the syringe can include an input interface for receiving identifying information about the components in the delivery path, and optionally the delivery target, to configure the operation of the compensation circuit and/or a threshold warning system. The indentifying information can be provided/selected by a user or received via a mechanical, wired, or wireless interface from the delivery path, and optionally the delivery target.

In another embodiment, the syringe can include a plunger with a plunger tip, and the volume sensor can include a linear potentiometer having its slider coupled to the plunger tip. Therefore, as the plunger is depressed into the reservoir, the slider of the linear potentiometer moves in concert with the plunger tip, thereby providing an indication of the displacement of the plunger tip. This displacement can be multiplied by the cross-sectional area of the reservoir to determine the volume of flowable material dispensed from the reservoir.

In another embodiment, a surgical procedure can be performed by delivering flowable material from a reservoir through a delivery path to a delivery target, measuring the dispensed volume of flowable material from the reservoir, measuring a pressure applied to the flowable material, and calculating a delivered volume of flowable material at the delivery target by determining the interior volume of the delivery path at the measured pressure and subtracting that value from the dispensed volume measurement.

As will be realized by those of skilled in the art, many different embodiments of an introducer/guide pin device, systems, kits, and/or methods of using an introducer/guide pin device according to the present invention are possible. Additional uses, advantages, and features of the invention are set forth in the illustrative embodiments discussed in the detailed description herein and will become more apparent to those skilled in the art upon examination of the following.

BRIEF DESCRIPTION OF THE DRAWINGS

FIG. 1B is a system or kit that includes the syringe of FIG. 1A.

FIGS. 4A-4C show an exemplary volume sensor that includes a linear potentiometer for use with the syringe of FIG. 1A

DETAILED DESCRIPTION

By incorporating compensation logic into a material delivery system that accounts for system compliance, material delivery during surgical procedures can be accurately determined.

Figure 1A:
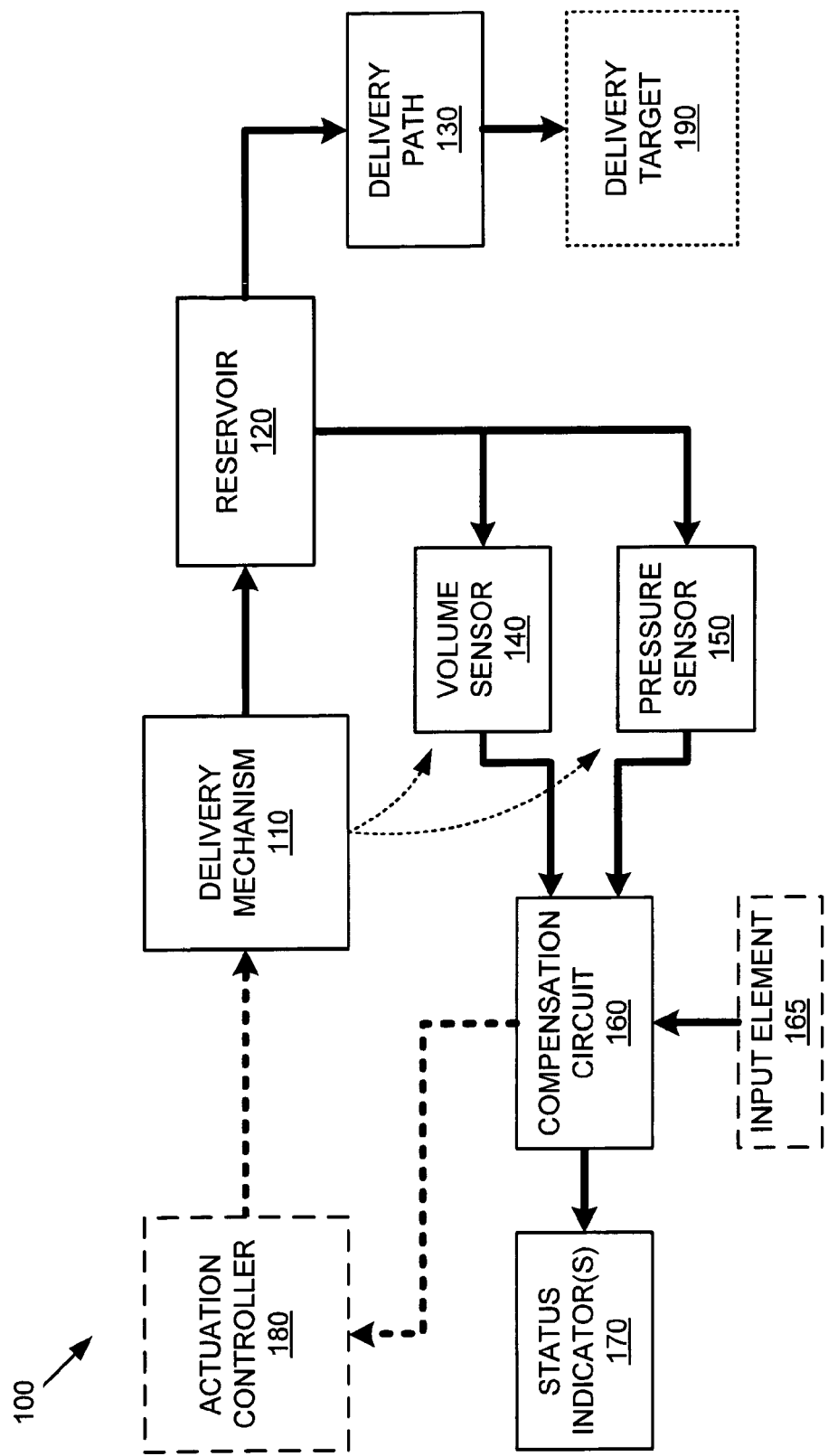
FIG. 1A is a block diagram of a syringe that includes a compensation circuit that accounts for system compliance to accurately determine actual material delivery volume.

FIG. 1 shows a block diagram of a syringe 100 of that can be used to deliver a flowable material to a delivery target 190 (e.g., an expandable device or a body part) during a surgical procedure. Syringe 100 includes a delivery mechanism 110 that expresses the flowable material from a reservoir 120 through a delivery path 130 to delivery target 190. A volume sensor 140 measures the amount of material dispensed from reservoir 120 ("dispensed volume"), and a pressure sensor 150 measures the system pressure being applied to deliver the flowable material to delivery target 190.

Note the volume sensor 140 can be any type of sensor that can determine, or can be used to determine, the amount of material dispensed from reservoir 120. For example, volume sensor 140 can be a flow meter that provides a total volume flow indication. However, such sensors can be expensive and are sometimes unsuitable for lower cost syringe designs. In various other embodiments, a lower cost optical or magnetic sensor could be used to measure the displacement of the plunger, so that the dispensed volume could be calculated by multiplying the displacement by the cross-sectional area of the reservoir.

In another embodiment, a linear potentiometer can be used to measure the dispensed volume, as shown in FIGS. 4A and 4B. In many instances, a linear potentiomer is an attractive component, due to its low power requirements and its ability to retain its measurement values when powered off. FIG. 4A shows an embodiment of syringe 100 that includes a plunger 110 (delivery mechanism) that includes a handle 111 and a plunger tip 112 that is slidably placed in a reservoir 120. Syringe 100 further includes a volume sensor 140 that includes a linear potentiometer 441 aligned with the side of reservoir 120 (i.e., the axis of motion of a slider 442 of linear potentiometer 441 is substantially parallel to an axis of motion of plunger 110 within reservoir 120).

Volume sensor 140 further includes a cable coupled between slider 442 and plunger tip 112 via a port at the rear (plunger side) of reservoir 120, and a biasing element 443 (e.g., a spring, elastic element, or any other resilient element) for moving slider 442 to a default position. Therefore, as handle 111 is depressed to force plunger 110 further into reservoir 120 and express flowable material 209 into tubing 131, plunger tip 112 pulls cable 445 into reservoir 120, as shown in FIG. 4B. Cable 445 pulls slider 442 away from its default position, thereby changing the resistance of linear potentiometer 441 and allowing the displacement of plunger tip 112 to be calculated. This displacement can be multiplied by the cross-sectional area of reservoir 120 to determine the amount of flowable material 209 dispensed from reservoir 120. In some embodiments, this dispensed volume determination can further include a compensation factor to account for any non-linearity in linear potentiometer 140, thereby enhancing measurement accuracy.

Note that while biasing element 443 is depicted as being coupled to slider 442 on the opposite side of cable 445, in various other embodiments, biasing element can be coupled to the same side of slider 442 as cable 445. In various other embodiments, biasing element 443 can be eliminated completely, if the need for automatic "resetting" of linear potentiometer 441 is not required. In some embodiments, reservoir 120 can have a non-circular cross section (e.g., oval) to prevent twisting of cable 445 around plunger 110.

Figure 4C:
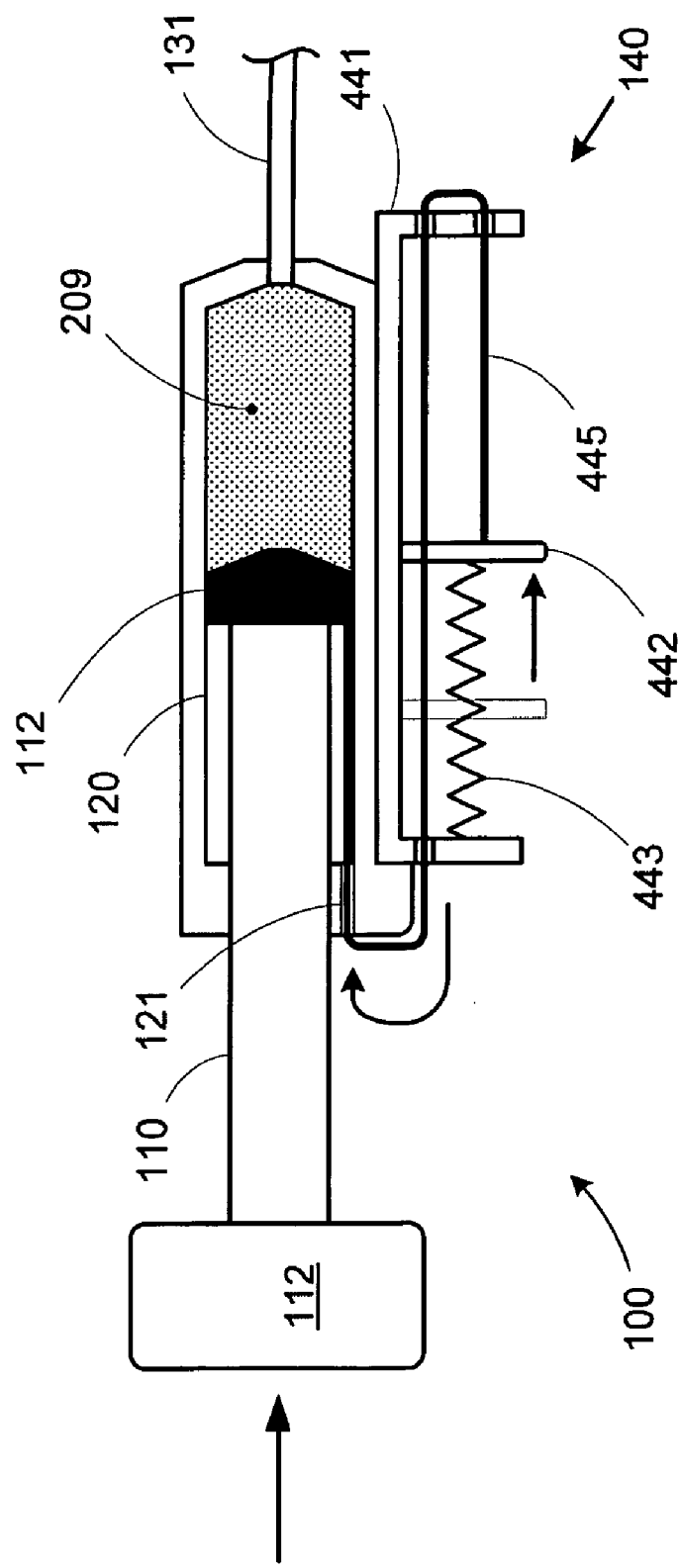

Note further that although slider 442 is depicted as moving in the opposite direction as plunger tip 112, in various other embodiments, cable 121 can be routed such that slider 442 moved in the same direction as plunger tip 112. For example, FIG. 4C shows an alternative embodiment of syringe 100 in which cable 445 runs completely across linear potentiometer 441 and loops back to be coupled to slider 442. As a result, pushing plunger tip 112 into reservoir 120 this time causes slider 442 to move in the same direction as plunger tip 112. Various other ways of coupling plunger tip 112 to slider 442 will be readily apparent.

Note further that while a cable connection between plunger 110 and slider 442 is depicted and described for exemplary purposes, in various other embodiments, other types of connections can be used. For example, in one embodiment, plunger 110 (or handle 112) can be connected to slider 442 by a rigid follower (e.g., a rod, beam, or other rigid element that moves slider 442 in unison with plunger 110).

Returning to FIG. 1A, in various embodiments, volume sensor 140 and pressure sensor 150 can take readings at or on reservoir 120. For instance, pressure sensor 150 could be mounted on the wall of reservoir 120, and volume sensor 140 could be a flow meter located at or around the outlet of reservoir 120 (e.g., where deliver path 130 meets reservoir 120). However, in various other embodiments, volume sensor 140 and/or pressure sensor 150 can perform their measurements at or on delivery mechanism 110. For example, pressure sensor 150 could be mounted on the tip of a plunger in delivery mechanism 110, and volume sensor 140 could be a position sensor for measuring the displacement of the plunger tip. Various alternative sensor placements will be readily apparent.

The higher the pressure used to deliver the flowable material, the more the system components exposed to that pressure will deform (i.e., expand). This expansion can occur in reservoir 120, but typically is more significant in delivery path 130, which often includes flexible tubing and/or small catheters to carry the flowable material through a narrow cannula to delivery target 190. In any case, this system compliance can result in significant differences between the expected volume of material delivered to delivery target 190 (i.e., the volume of material expressed from reservoir 120 minus the (unpressurized) volume of delivery path 130) and the actual volume of material delivered.

To overcome this measurement inaccuracy, syringe 100 further includes a compensation circuit 160 that determines an actual material delivery volume and provides that information to one or more status indicators 170 (e.g., digital display, gauge, graphical indicators, tactile outputs, aural outputs, etc.) that provide an indication of that actual material delivery volume. Specifically, compensation circuit 160 takes the measured volume read by volume sensor 140, and adjusts that value based on a pressure reading from pressure sensor 150, and provides the adjusted value to status indicator 170 for display.

Note that the volumetric compensation capability can be provided in any number of ways. For example, in one embodiment, compensation circuit 160 can include a lookup table that stores the volumetric changes in or total volume of reservoir 120 and/or delivery path 130 at various pressures. Compensation circuit 160 can then use the stored value corresponding to the pressure value provided by volume sensor 140 to appropriately modify the delivery volume provided by volume sensor 140 to generate the adjusted delivery volume.

In another embodiment, compensation circuit 160 can include a mathematical model of reservoir 120 and/or delivery path 130 that can be used to calculate a volumetric change or total volume based on the pressure value provided by pressure sensor 150. Various other embodiments will be readily apparent.

In various embodiments, compensation circuit 160 can be implemented as hardware (e.g., an ASIC, EEPROM, or FPGA, among others), software, or a combination of the two. Compensation circuit 160 can be physically integrated with the mechanical elements of syringe 100, or may only be connected via a data link (e.g., wired or wireless connection).

In one embodiment, compensation circuit 160 can include an optional input element 165 that provides compensation circuit 160 with information about the physical characteristics of reservoir 120 and/or delivery path 130. This can enable syringe 100 to accommodate multiple different reservoir/deliver path combinations and still provide accurate determination of the actual material delivery volume provided to delivery target 190.

For example, in one embodiment, delivery path 130 could be selected from a set of structures having different physical characteristics (e.g., a set of inflatable bone tamps having different balloon configurations and sizes). Compensation circuit could include multiple lookup tables or mathematical models corresponding to the different delivery path structures, and the relevant lookup table or model to be used by compensation circuit 160 could be selected via input element 165. In one embodiment, input element 165 could be a manual entry system (e.g., a button(s), dial(s), knob(s), switch(es), keypad, or any other user interface) that allows a user to indicate the system parameters to be used by compensation circuit 160 (e.g., if a size 3 inflatable bone tamp is to be used in delivery path 130 and delivery target 190, the user could select the size 3 setting using input element 165).

In other embodiments, input element 165 could be a detection system that automatically identifies at least one component of delivery path 130 and delivery target 190 (e.g., via mechanical interface, electrical/optical/magnetic/RF/IR or other analog or digital signal, etc.) and causes compensation circuit 160 to operate accordingly. For example, a size 2 inflatable bone tamp could include an RFID tag (either active or passive) for transmitting a "size 2" signal, and input element 165 could include an antenna and reader for receiving that signal and providing the information to compensation circuit 160. Various other control/input systems will be readily apparent.

In some embodiments, syringe 100 can include an optional actuation controller 180 that controls delivery mechanism 110 based on the material delivery volume value determined by compensation circuit 160. For instance, when a threshold material delivery volume (based on the value provided by compensation circuit 160) or threshold delivery pressure (based on the value provided by pressure sensor 150) is reached, actuation controller 180 stop delivery mechanism 110, thereby preventing overfilling or overpressurizing, respectively, delivery target 190. In some embodiments, actuation controller 180 can control the actuation of delivery mechanism 110 as well, thereby providing closed loop control over the operation of syringe 100 (e.g., actuation controller 180 actuates delivery mechanism 110 to dispense filler material into delivery target 190 until compensation circuit 160 indicates that the threshold delivery volume has been reached).

FIGS. 2B-2G show an exemplary use of syringe 100 in the performance of a minimally invasive surgical procedure. FIG. 2A shows a portion of a human vertebral column having vertebrae 201, 202, and 203. Vertebra 202 has collapsed due to a vertebral compression fracture (VCF) 202-F that could be the result of osteoporosis or cancer-related weakening of the bone. The abnormal curvature of the spine caused by VCF 202-F can lead to severe pain and further fracturing of adjacent vertebral bodies.

One treatment for this type of fracture is to perform a minimally invasive procedure in which a reinforcing bone filler material is injected into the fractured vertebra, either directly into the fractured region (vertebroplasty) or into a cavity created beforehand in the cancellous bone structure (kyphoplasty). Kyphoplasty is often a preferred technique due to the potential height restoration that can be achieved during the cavity creation phase of the procedure.

Figure 2B:
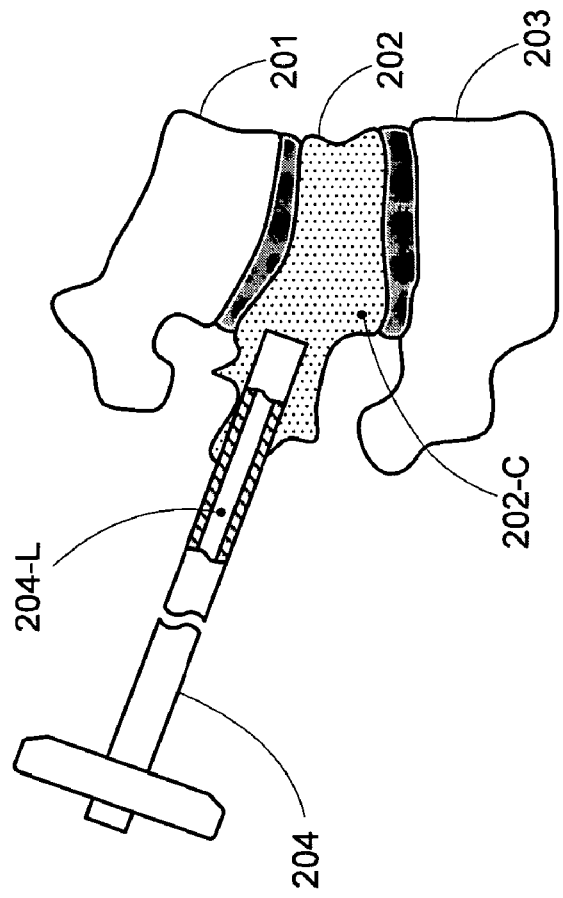
FIGS. 2A-2G shows an exemplary use of the syringe of FIG. 1A to perform a surgical procedure.
Figure 2A:
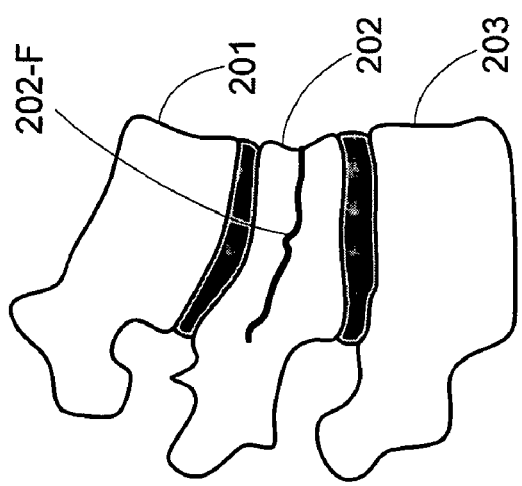

FIG. 2B shows a cannula 204 being positioned next to the target surgical location, which in this case is the cancellous bone structure within fractured vertebra 202. In this manner, a percutaneous path to vertebra 202 is provided via an interior lumen 204-L of cannula 204. Typically, cannula 204 is docked into the exterior wall of the vertebral body (using either a transpedicular or extrapedicular approach) using a guide needle and/or dissector, after which a drill or other access tool (not shown) is used to create a path further into the cancellous bone 202-C of vertebra 202. However, any other method of cannula placement can be used to position cannula 204.

Figure 2C:
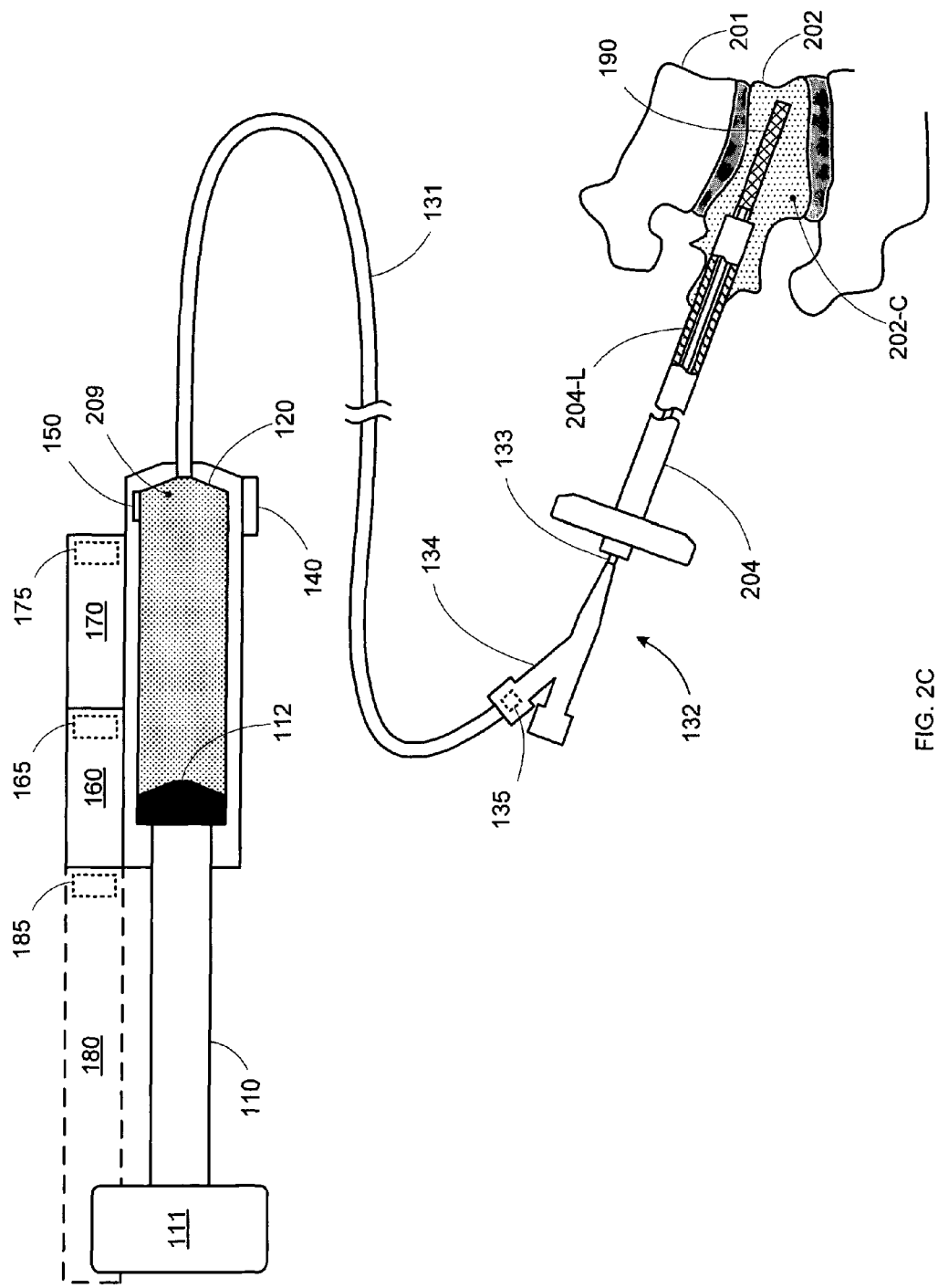

Then in FIG. 2C, an inflatable bone tamp 132 is placed into cannula 204. Inflatable bone tamp 132 includes a shaft 133 (e.g., a catheter), an expandable structure 190 (e.g., a balloon) at the distal end of shaft 133, and a connector 134 (e.g., a Luer Lock fitting) at the proximal end of shaft 133. Inflatable bone tamp 132 is coupled to syringe 100 by a flow channel 131 (e.g., flexible tubing). Thus, delivery path 130 as described in FIG. 1A would include flow channel 131, connector 134, and shaft 133, while expandable structure 190 is the inflation target.

Syringe 100 includes a reservoir 120 and a plunger 110. Plunger 110 includes a handle 111 and a plunger tip 112 that is slidably disposed in reservoir 120. As described with respect to FIG. 1A, syringe 100 further includes a volume sensor 140, a pressure sensor 150, a compensation circuit 160, a status indicator 170, and an optional actuation controller 180. Note that while plunger handle 111 is depicted as having a T-handle or knob for exemplary purposes, in various other embodiments, handle 111 can be a trigger, ratchet, lever, linkage, or any other structure or mechanism for moving plunger tip 112 within reservoir 120.

Figure 2D:
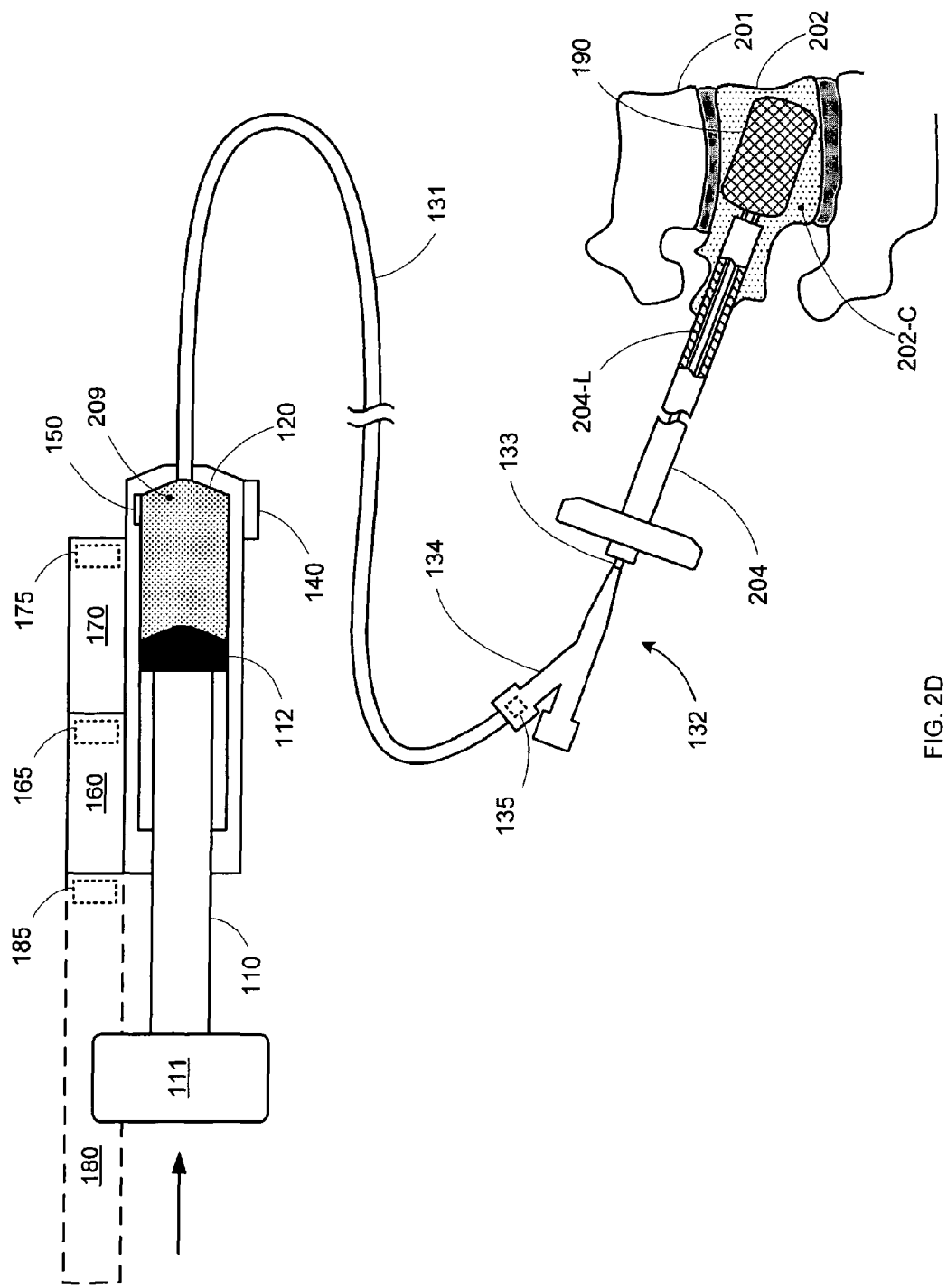

To inflate expandable structure 190, a force is applied to handle 111 that drives plunger tip 112 through reservoir 120, thereby expressing flowable material 209 through flow channel 131, connector 134, and shaft 133, and into expandable structure 190. The resulting expansion of expandable structure 190 compresses the surrounding cancellous bone 202-C to create a well-defined cavity within fractured vertebra 202, and can also restore some or all of the original height of the vertebral body, as shown in FIG. 2D.

As described above with respect to FIG. 1A, as syringe 100 delivers flowable material 209 to expandable structure 190, volume sensor 140 and pressure sensor 150 monitor the volume of material 209 being dispensed from reservoir 120 (i.e., the dispensed volume) and the pressure being applied to material 209, respectively. As also noted above with respect to FIG. 1A, volume sensor 140 can be any sensor that determines, or enables the determination of, the volume of flowable material 209 that is dispensed from reservoir 120 (e.g., a flow meter, an optical or magnetic sensor for measuring the change in position of plunger tip 112, or a linear potentiometer that is coupled to plunger 110 such that motion of plunger tip 112 moves the slider of the linear potentiometer, among others).

Using the dispensed volume and pressure values provided by volume sensor 140 and pressure sensor 150, respectively, compensation circuit 160 determines the actual volume of flowable material delivered to expandable structure 190 (i.e., the delivered volume), and this information is provided to the user by status indicator 170. In some embodiments, status indicator 170 can be a digital or analog display of the actual delivered volume (i.e., numerical value) generated by compensation circuit 160. In other embodiments, status indicator can be a graphical representation of the actual delivered volume (e.g., a series of LEDs (light emitting diodes) that light up as the volume of flowable material 209 in expandable structure 190 increases).

In some embodiments, status indicator 170 can include a limit indicator 175 that provides a warning when a threshold delivered volume or pressure is reached. For example, it may be desirable to warn a user an overfill or overpressure condition is close to being reached. Towards this end, limit indicator 175 could provide a visual indicator (e.g., flashing light), aural indicator (e.g., buzzer or chime), or tactile indicator (e.g., vibration) when a predetermined threshold pressure value is measured by pressure sensor 150 or a predetermined threshold delivered volume value is generated by compensation circuit 160. In certain embodiments, a tactile warning provided by limit indicator 175 could enhance the usability of such a warning system by alerting a user without requiring the user to actually look at the syringe. In various embodiments, settings for limit indicator 175 can be input by the user, can be preprogrammed into limit indicator 175, or any combination of the two. In various other embodiments, limit indicator 175 could automatically detect the settings via a wireless data protocol (e.g., RFID, WiFi, IR, Bluetooth, etc.).

As noted above, compensation circuit 160 determines the actual volume of flowable material present in the delivery path (e.g., the internal volume of flow channel 131, connector 134, and shaft 133) as those elements within the delivery path expand due to increased pressure from plunger 110. This actual delivery path volume can then be subtracted from the volume measurement taken by volume sensor 140 (i.e., the dispensed volume) to determine the true delivered volume of flowable material 209 at expandable structure 190.

As noted above with respect to FIG. 1A, compensation circuit 160 can be hardware (e.g., integrated circuit or programmable logic), software, or any combination of the two. Likewise, the determination of the internal volume of the delivery path at a given pressure can be performed via one or more lookup tables, a mathematical model of the delivery path, or a combination of the two (e.g., coefficients of expansion for the various components of the delivery path can be extracted from lookup tables, and those coefficients of expansion can be plugged in to an expression of interior volume that is a function of pressure). Various other techniques for determining the interior volume of the delivery path at a given pressure will be readily apparent.

In some embodiments, syringe 100 can be configured to be used with a specific delivery path (e.g., a specific size and length of flow channel 121 and a specific size and type of inflatable bone tamp 132). However, as noted above, in various other embodiments, compensation circuit 160 can include an input element 165 through which information about the particular delivery path being used can be provided to compensation circuit 165.

In one embodiment, input element 165 can be a manual entry device (e.g., a button(s), dial(s), knob(s), switch(es), keypad, or any other user interface) that allows a user to identify the components in the delivery path. In another embodiment, input element 165 can be an automatic detection device (e.g., a sensor, receiver, or other data input interface) that automatically identifies the components in the delivery path and/or delivery target, via a mechanical interface, a wired interface, or a wireless interface. For example, inflatable bone tamp 132 can include an indicator element tag 135, such as an RFID tag, identifying markings or features, or any other element that can be read or detected by input element 165 to provide compensation circuit 160 with the characteristics (size, type, operating limits, etc.) of inflatable bone tamp 132.

In another embodiment, syringe 100 can include an actuation controller 180 that can control the delivery of flowable material 209 from reservoir 120. In one embodiment, actuation controller 180 can comprise a threshold limiter 185 that stops delivery of flowable material 209 when the delivered volume in expandable structure 190 reaches a predetermined value. For example, threshold limiter 185 can be a clamp, lever, latch, or other mechanism that locks plunger 110 in place when compensation circuit 180 detects that the delivered volume of flowable material 209 has reached a predetermined limit. In another embodiment, actuation controller 180 can include a linear actuator or other mechanism to depress plunger 110 into reservoir 120 until threshold limiter 185 detects the desired delivery volume value from compensation circuit 180. Various other actuator/limiter combinations will be readily apparent.

Figure 2E:
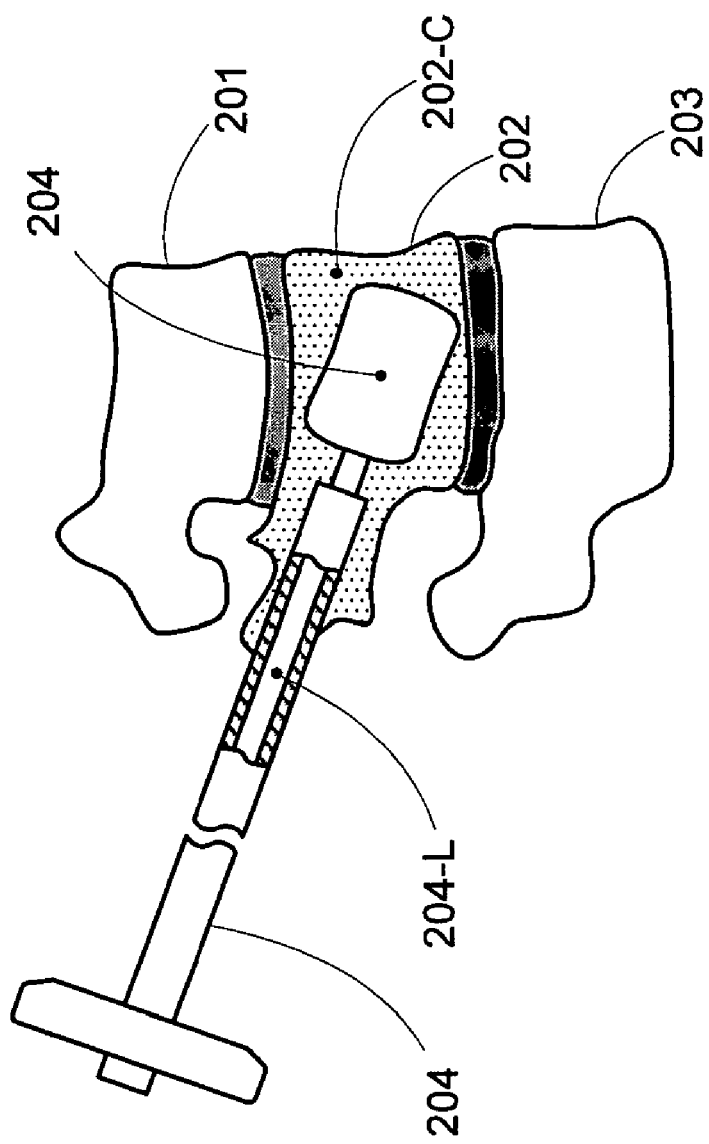
Figure 2F:
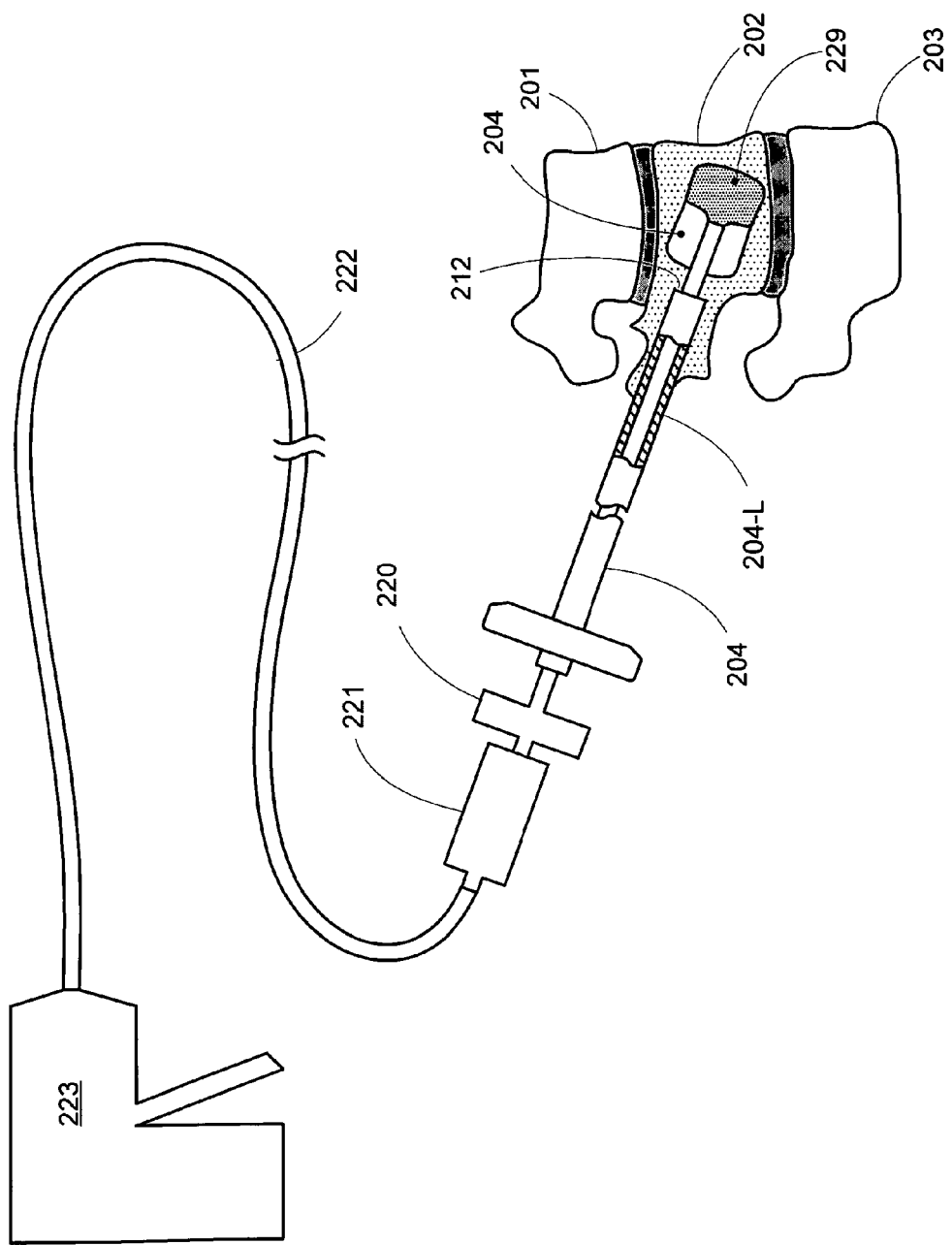
Figure 2G:
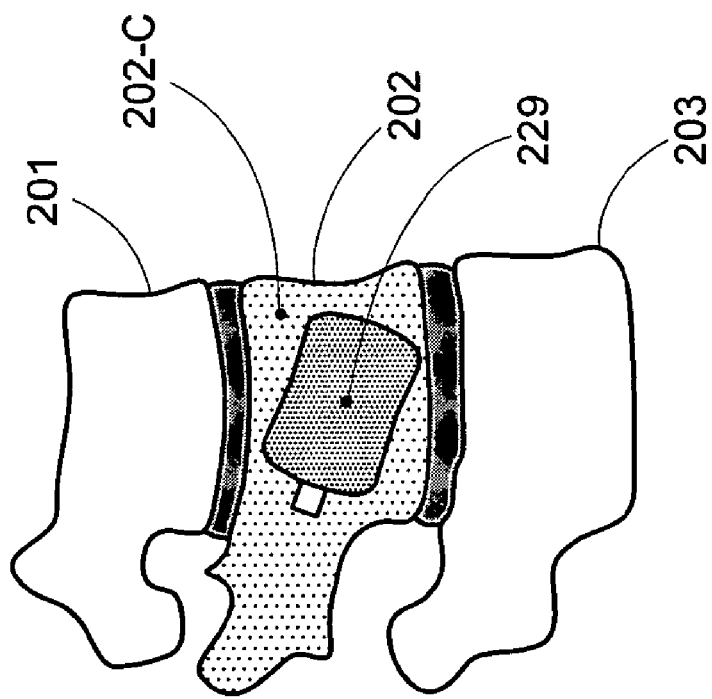

Once expandable structure 190 has been expanded to a desired volume, it is contracted and removed from vertebra 202 through cannula 204. As shown in FIG. 2E, the result of the previously described expansion procedure is a well-defined cavity 204 in cancellous bone 202-C. Cavity 204 can then be filled with bone filler material 229 (e.g., PMMA), as shown in FIG. 2F. A delivery nozzle 220 is inserted through cannula 204 and into cavity 204, and is used to direct bone filler material 229 into cavity 204.

As shown in FIG. 2F, in one embodiment, a quantity of bone filler material 229 can be housed in a cartridge 221 attached to delivery nozzle 220. A hydraulic actuator 223 can then be used to remotely express bone filler material 229 from cartridge 221 via a hydraulic line 222 (e.g., cartridge 221 can include a piston that is driven by the hydraulic pressure supplied by hydraulic line 222). Note, however, that in various other embodiments, bone filler material 229 can be delivered to cavity 204 in any number of different ways (e.g., a high pressure cement delivery pump that delivers the cement to nozzle 220 through a flexible line, or a syringe or other delivery device filled with bone filler material 229 that is attached directly to nozzle 220).

Once the filling operation is complete, delivery nozzle 220 and cannula 204 are removed from vertebra 202 (and the patient's body) as shown in FIG. 2F. Upon hardening, bone filler material 229 provides structural support for vertebra 202, thereby substantially restoring the structural integrity of the bone and the proper musculoskeletal alignment of the spine. In this manner, the pain and attendant side effects of a vertebral compression fracture can be addressed by a minimally invasive kyphoplasty procedure. Note that although the use of syringe 100 is described with respect to a kyphoplasty procedure for exemplary purposes, syringe 100 can be used in any procedure in which accurate determination of actual delivered material volume is beneficial (e.g., in the distraction, displacement, and/or repositioning/alignment of long bones, or any other body parts).

Figure 3:
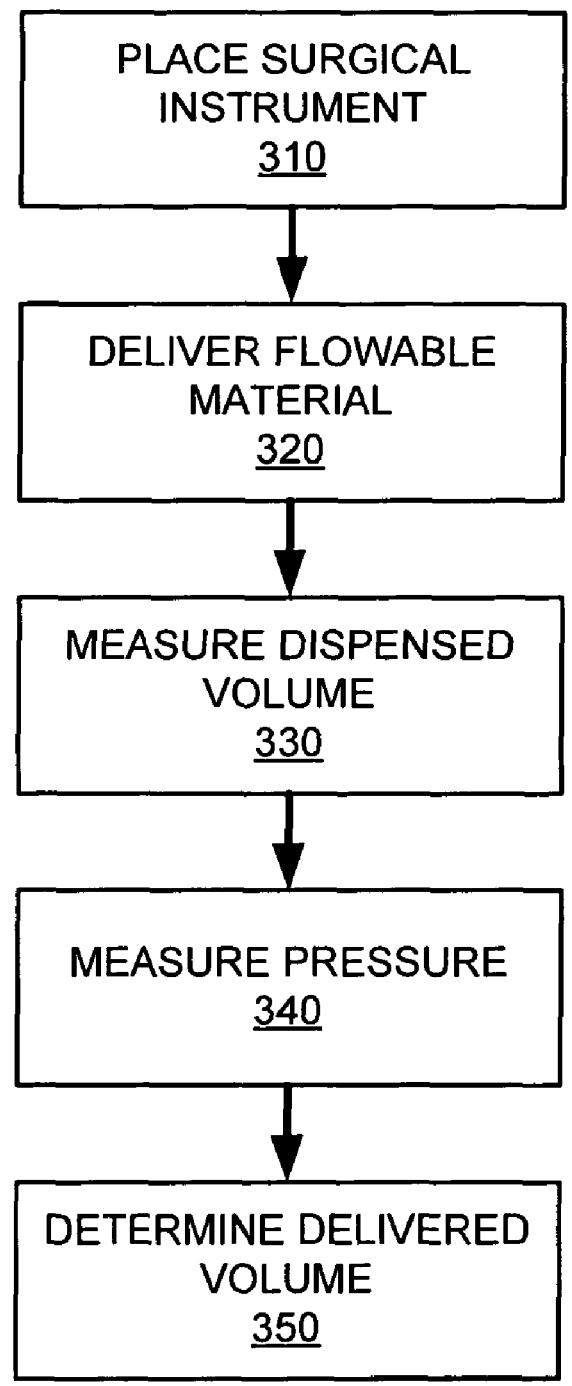
FIG. 3 is a flow diagram for a surgical procedure using the syringe of FIG. 1A.

FIG. 3 shows a flow diagram of a process for performing a surgical procedure using a high-pressure delivery device as described with respect to FIGS. 1A-1B and 2A-2G. In a PLACE SURGICAL INSTRUMENT step 310, a surgical instrument is placed within a patient, such as described with respect to FIGS. 2A-2C. Then, in a DELIVER FLOWABLE MATERIAL step 320, a flowable material is delivered to the surgical instrument from a reservoir, as described with respect to FIGS. 2C-2D.

In a MEASURE DISPENSED VOLUME step 330, the volume of flowable material dispensed from the reservoir is measured, and in a MEASURE PRESSURE step 340, the pressure being applied to the flowable material is measured. These two measurements are then used in a DETERMINE DELIVERED VOLUME step 350 to calculate the actual volume of flowable material delivered to the surgical instrument, taking in to account system compliance and response to the pressure being applied to the flowable material, as described with respect to FIGS. 1A and 2D. Note that although steps 330 and 340 are depicted as being sequential steps in FIG. 3 for exemplary purposes, in various other embodiments steps 330 and 340 can be performed in reverse order, concurrently, periodically, or in any manner that provides the appropriate pressure and volume values for use in step 350.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A method for delivering a flowable material through a delivery path to a surgical delivery target, the method comprising:
   providing a syringe comprising:
      a reservoir for holding a flowable material;
      an actuator for dispensing the flowable material from the reservoir into a delivery path and to a delivery target;
      a volume sensor to measure a first value for a first volume of flowable material dispensed from the reservoir;
      a pressure sensor to measure a pressure applied to the flowable material; and a compensation circuit to adjust the first value for the first volume based on the pressure to determine a second volume of flowable material delivered to the delivery target;

measuring a first volume of the flowable material dispensed from the reservoir;

measuring a pressure applied to the flowable material; and determining an actual volume of the flowable material delivered to the surgical delivery target based on the pressure and the first volume of flowable material.

2. The method of claim 1, wherein determining the actual volume comprises: determining an interior volume of the delivery path at the pressure; and subtracting the interior volume from the first volume.

3. The method of claim 1, further comprising providing a warning when the pressure reaches a threshold pressure value or when the actual volume reaches a threshold volume value.

4. The method of claim 3, wherein the warning is at least one of a visual, aural, or tactile indication.

5. The method of claim 1, further comprising providing a user interface to allow input regarding at least one of the delivery path and the delivery target.

6. The method of claim 1, further comprising automatically identifying at least one component of the delivery path and delivery target by providing a detection system in the compensation circuit.

7. The method of claim 6, further comprising receiving identification information about the at least one of the delivery path and the delivery target over a wireless protocol provided in a receiver in the detection system.

8. The method of claim 1, further comprising controlling the actuator in response to the second volume of flowable material determined by and actuation controller in the compensation circuit.

9. The method of claim 8, further comprising controlling the actuation controller stopping the actuator when the pressure reaches a threshold pressure value or when the second volume reaches a threshold volume value.

10. The method of claim 1, further comprising correlating a range of values for the pressure with a corresponding range of values for the interior volume of the delivery path by use of a lookup table in the compensation circuit.

* * * * *